United States Patent [19]

Grollier et al.

[11] Patent Number: 4,876,085
[45] Date of Patent: Oct. 24, 1989

[54] COSMETIC COMPOSITION CONTAINING OXATHIAZINONES

[75] Inventors: Jean F. Grollier; Chantal Fourcadier, both of Paris, France

[73] Assignee: L'Oreal, Paris, France

[21] Appl. No.: 864,573

[22] Filed: May 19, 1986

Related U.S. Application Data

[63] Continuation of Ser. No. 608,910, May 10, 1984, abandoned.

[30] Foreign Application Priority Data

May 11, 1983 [LU] Luxembourg .................... 84800

[51] Int. Cl.⁴ .................... A61K 7/06; A61K 7/07; A61K 7/42; A61K 9/12
[52] U.S. Cl. .................... 424/47; 8/405; 8/406; 424/DIG. 1; 424/DIG. 2; 424/59; 424/60; 424/69; 424/70; 424/71; 424/72; 424/74; 514/844; 514/846; 514/847; 514/937; 514/944; 514/945
[58] Field of Search .................... 424/59, 70, 47, 59, 424/60

[56] References Cited

U.S. PATENT DOCUMENTS

| | | | |
|---|---|---|---|
| 2,146,646 | 2/1939 | Nüsslein et al. | 544/2 |
| 2,886,488 | 5/1959 | Berg et al. | 424/DIG. 4 |
| 2,901,399 | 8/1959 | Clarey | 424/DIG. 4 |
| 3,231,580 | 1/1966 | Mannheimer | 544/2 |
| 3,235,549 | 2/1966 | Broussalian | 544/2 |
| 3,344,174 | 9/1967 | Broussalian | 544/2 |
| 3,689,485 | 9/1972 | Clauss et al. | 544/2 |
| 3,689,486 | 9/1972 | Clauss et al. | 544/2 |
| 3,839,571 | 10/1974 | Ciccone | 424/DIG. 4 |
| 3,926,976 | 12/1975 | Clauss et al. | 260/243 R |
| 3,926,981 | 12/1975 | Clauss et al. | 260/243 R |
| 3,968,106 | 7/1976 | Clauss et al. | 260/243 R |
| 3,968,107 | 7/1976 | Clauss et al. | 260/243 R |
| 3,969,348 | 7/1976 | Pietsch et al. | 260/243 R |
| 4,166,177 | 8/1979 | Cragol, Jr. et al. | 544/2 |

FOREIGN PATENT DOCUMENTS

| | | | |
|---|---|---|---|
| 8480 | 5/1980 | European Pat. Off. | 424/49 |
| 2456874 | 6/1976 | Fed. Rep. of Germany | 424/DIG. 4 |
| 2141948 | 1/1973 | France | 544/2 |
| 2187793 | 1/1974 | France | 424/316 |
| 2278690 | 7/1975 | France | 424/316 |
| 2315907 | 1/1977 | France | 424/53 |
| 1340911 | 12/1973 | United Kingdom | 544/2 |

Primary Examiner—Dale R. Ore
Attorney, Agent, or Firm—Fleit, Jacobson, Cohn, Price, Holman & Stern

[57] ABSTRACT

A cosmetic composition for overcoming the greasy and unattractive look of hair and skin, comprising at least one oxathiazinone derivative of the formula:

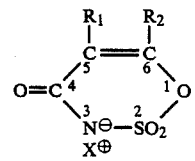

in which $R_1$ denotes hydrogen, alkyl, aryl or acyl; $R_2$ denoted alkyl or aryl; or alternatively $R_1$ and $R_2$, together with the carbon atoms to which they are attached, form an alicyclic radical; and X denotes an alkali metal, together with at least one cosmetic adjuvant.

46 Claims, No Drawings

COSMETIC COMPOSITION CONTAINING OXATHIAZINONES

This application is a continuation of application Ser. No. 608,910, filed May 10, 1984, now abandoned.

This invention relates to a cosmetic composition containing at least one oxathiazinone derivative for treating the hair or skin.

The hair or skin of certain people may have a greasy and unattractive look due to excessive secretion from the sebaceous glands.

It has been discovered that, surprisingly, certain oxathiazinone derivatives combat the greasy look of the hair and improve its appearance.

It has also been discovered that these oxathiazinone derivatives combat the greasy and unattractive look of the skin and thereby improve its appearance.

The invention thus provides a cosmetic composition suitable for treating the hair or skin which comprises at least one oxathiazinone derivative of the formula:

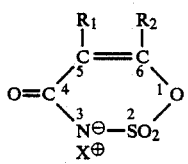

(I)

in which $R_1$ denotes a hydrogen atom, an alkyl radical having from 1 to 20 carbon atoms, an aryl radical having up to 10 carbon atoms or an acyl radical $R_3CO$, in which $R_3$ is an alkyl radical having from 2 to 4 carbon atoms; $R_2$ denotes an alkyl radical having from 1 to 20 carbon atoms or an aryl radical having up to 10 carbon atoms; or alternatively $R_1$ and $R_2$ together with the carbon atoms to which they are attached form an alicyclic radical having up to 10 carbon atoms, which is optionally substituted by one or more hydrocarbon radicals; and X denotes an alkali metal, preferably potassium, together with one or more cosmetic adjuvants.

Cosmetic adjuvants are selected from the group comprising non-ionic, anionic, cationic, amphoteric surface active agents and mixtures thereof, cosmetic polymers, preservatives, sequestering agents, thickeners, softeners, foam synergistic agents, foam stabilizers, sun filters, peptizing agents, colourants, pigments, fatty alcohols, waxes, humectants, perfumes.

The oxathiazinone derivatives of formula (I) may be prepared by the process described in British Pat. No. 1,340,911, French Pat. Nos. 2,231,676, 2,187,793, 2,278,690 and 2,278,691, U.S. Pat. Nos. 3,926,981, 3,926,976, 3,968,106, 3,968,107 and 3,969,348 or West German Pat. Nos. 2,228,423, 2,327,804, 2,434,549, 2,434,562 and 2,434,564.

The compositions according to the invention are applied topically, i.e. they must be applied to the hair or to the skin.

The invention also provides a cosmetic process for combating the effects of excessive secretion from the sebaceous glands, which comprises applying an effective quantity of a composition as defined above to the hair or skin.

The invention also provides a method for the treatment of the hair or of the skin which comprises applying, to the hair or to the skin, an appropriate amount of a composition as defined above.

Preferably oxathiazinone derivatives of formula (I) are used in which $R_1$ denotes hydrogen or an alkyl radical having from 1 to 4 carbon atoms and preferably $R_2$ denotes an alkyl radical having from 1 to 4 carbon atoms. More preferably one uses the compound of formula (I) in which $R_1$ denotes hydrogen, $R_2$ denotes $CH_3$ and X denotes potassium and which is sold by HOECHST under the trademark "ACESULFAME K" and the chemical name "Potassium salt of 6-methyl-1,2,3-oxathiazin-4(3H)-one-2,2-dioxide.

This invention also provides a cosmetic composition making it possible to combat the greasy and unattractive look of the hair and skin containing at least one oxathiazinone derivative of formula (I) in the form of an aqueous, alcoholic or aqueous-alcoholic suspension or solution, and alcohol having from 1 to 4 carbon atoms; or in the form of an emulsion, a gel or a powder. The composition can be packaged as an aerosol. Ethanol or isopropyl alcohol are preferred among the alcohols. If the vehicle is a mixture of water and alcohol, the alcohol is preferably present in a quantity of from 10 to 70% by weight, relative to the total weight of the composition.

The concentration of the oxathiazinone derivative of formula (I) is generally from 0.05 to 20% and preferably from 0.5 to 5% by weight relative to the total weight of the composition.

The compositions according to the invention can also contain one or more oxathiazinone derivatives of the formula (I) in a mixture with other known compounds for combating the greasy and unattractive look of the hair or skin.

If the compositions according to the invention are intended for treating the hair, these compositions include shampoos, rinse-off lotions, creams, shaping lotions such as setting lotions or blow-drying lotions, or lacquers, or in the form of treating products which can be applied before or after dyeing or bleaching, before or after shampooing or before or after permanent waving.

If the compositions for the hair, according to the invention are shampoos, they also contain one or more surface-active agents. These surface-active agents can be anionic, non-ionic, cationic, amphoteric or a mixture thereof.

Examples of anionic surface-active agents are alkali metal salts, the ammonium salts, the amine salts or the aminoalcohol salts of the following compounds:

alkyl-sulphates, alkyl-ether-sulphates, alkyl-amide-sulphates and alkylamide-ether-sulphates, alkylaryl-polyether-sulphates and monoglyceride-sulphates;

alkylsulphonates, alkylamidesulphonates, alkyl-aryl-sulphonates, α-olefinesulphonates and paraffinsulphonates;

alkyl-sulphosuccinates, alkyl-ether-sulphosuccinates and alkylamide-sulphosuccinates;

alkyl-sulphosuccinamates;

alkyl-sulphoacetates and alkyl-polyglycerol-carboxylates;

alkyl-phosphates and alkyl-ether-phosphates; and alkylsarcosinates, alkylpolypeptidates, alkylamidopolypeptidates, alkylisethionates and alkyltaurates, the alkyl radical in all these compounds preferably being a fatty chain containing from 12 to 18 carbon atoms; and fatty acids such as oleic acid, ricinoleic acid, palmitic acid, stearic acid and acids derived from copra oil or from hydrogenated copra oil.

acyllactylates in which the acyl radical contains from 8 to 20 carbon atoms; and carboxylic acids of polyglycol ethers, of the formula:

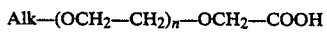
$$Alk-(OCH_2-CH_2)_n-OCH_2-COOH$$

or their salts, in which the substituent Alk represents a linear alkyl chain having from 12 to 18 carbon atoms and in which n is an integer from 5 to 15.

The anionic surface-active agents which are more particularly preferred are: the lauryl-sulphates of sodium, ammonium or triethanolamine, the sodium salt of sulphated lauryl alcohol oxyethyleneated with 2.2 mol of ethylene oxide, the triethanolamine salt of lauroylkeratinic acid and the triethanolamine salt of the condensation product of copra fatty acids with animal protein hydrolysates; and the compounds of the formula:

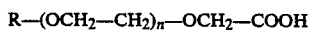
$$R-(OCH_2-CH_2)_n-OCH_2-COOH$$

in which R is an alkyl radical, preferably a $C_{12}$ to $C_{14}$ alkyl radical and n varies from 6 to 10.

Examples of non-ionic surface-active agents are:

polyoxyethyleneated, polyoxypropyleneated or polyglycerolated fatty alcohols, alkylphenols and acids with a fatty chain containing 8 to 18 carbon atoms; copolymers of ethylene oxide and propylene oxide, condensates of ethylene oxide and propylene oxide with fatty alcohols, polyoxyethyleneated fatty amides, polyoxyethyleneated fatty amines, ethanolamides, fatty acid esters of glycol, oxyethyleneated or non-oxyethyleneated fatty acid esters of sorbitan, fatty acid esters of sucrose, fatty acid esters of polyethylene glycols, phosphoric acid triesters, fatty acid esters derived from glucose, alkylglucosides and glycoside alkyl ethers.

the condensation products of a monoalcohol, an α-diol, an alkylphenol, an amide or a diglycolamide with glycidol, for example, the compounds of the formula:

$$R_4-CHOH-CH_2-O-(CH_2-CHOH-CH_2-O)_p-H$$

in which $R_4$ denotes an aliphatic, cycloaliphatic or arylaliphatic radical preferably having from 7 to 21 carbon atoms, and mixtures thereof, it being possible for the aliphatic chains to contain ether, thioether or hydroxymethylene groups, and in which p is from 1 to 10, such as the compounds described in French Pat. No. 2,091,516 or in U.S. Pat. No. 3,928,224;

compounds of the formula:

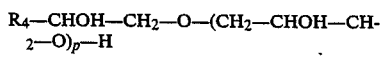
$$R_5O-[C_2H_3O-(CH_2OH)]_q-H$$

in which $R_5$ denotes an alkyl, alkenyl or alkylaryl radical and q has a statistical value of from 1 to 10 such as the compounds described in French Pat. No. 1,477,048 or in U.S. Pat. No. 3,578,719; and compounds of the formula:

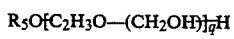
$$R_6-CONH-CH_2-CH_2-O-CH_2-CH_2-O-(CH_2-CHOH-CH_2-O)_r-H$$

in which $R_6$ denotes a linear or branched, saturated or unsaturated aliphatic radical, or a mixture of such radicals, which can optionally contain one or more hydroxyl groups, has from 8 to 30 carbon atoms and is of natural or synthetic origin, and r represents an integer or decimal number from 1 to 5 and denotes the average degree of condensation, such as the compounds de-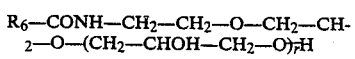scribed in French Pat. No. 2,328,763 or in U.S. Pat. No. 4,307,079.

Examples of non-ionic surface-active agents which are more particularly preferred are those of the formulae:

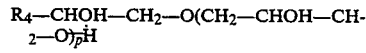
$$R_4-CHOH-CH_2-O(CH_2-CHOH-CH_2-O)_p-H$$

in which $R_4$ denotes a mixture of alkyl radicals having from 9 to 12 carbon atoms and p has a statistical value of about 3.5,

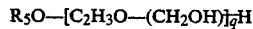
$$R_5O-[C_2H_3O-(CH_2OH)]_q-H$$

in which $R_5$ denotes $C_{12}H_{25}$ and q has a statistical value of 4 to 5, or

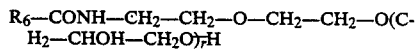
$$R_6-CONH-CH_2-CH_2-O-CH_2-CH_2-O(CH_2-CHOH-CH_2O)_r-H$$

in which $R_6$ denotes a mixture of radicals derived from lauric, myristic, oleic and copra acids and r has a statistical value of 3 to 4.

The preferred oxyethyleneated or polyglycerolated alkylphenols or fatty alcohols are oleyl alcohol oxyethyleneated with 10 mol of ethylene oxide, lauryl alcohol oxyethyleneated with 12 mol of ethylene oxide, nonylphenol oxyethyleneated with 9 mol of ethylene oxide, oleyl alcohol glycerolated with 4 mol of glycerol and sorbitan monolaurate oxyethyleneated with 20 mol of ethylene oxide.

Examples of cationic surface-active agents are:

fatty amine salts such as alkylamine acetates, quaternary ammonium salts such as alkyldimethylbenzylammonium, alkyltrimethylammonium, dialkyldimethylammonium, alkyldimethylhydroxyethylammonium and dimethyldistearylammonium chlorides or bromides, alkylamidoethyltrimethylammonium methosulphates in which the alkyl radicals preferably have from 1 to 22 carbon atoms, quaternary gluconamide halides such as those described in U.S. Pat. No. 3,766,267, quaternary halides of mink oil amides, such as those described in U.S. Pat. No. 4,012,398, quaternary derivatives of dialkylaminopropylamide fatty halogenoalkanoates, such as those described in U.S. Pat. No. 4,038,294, quaternary ammonium derivatives of lanoline fatty acids, such as those described in U.S. Pat. No. 4,069,347, alkylpyridinium salts and imidazoline derivatives; amine oxides, for example alkyldimethylamine oxides or alkylaminoethyldimethylamine oxides.

Examples of amphoteric surface-active agents are: alkylamino monopropionates and dipropionates, betaines such as N-alkylbetaines, N-alkylsulphobetaines and alkylamidobetaines, cycloimidinium compounds such as alkylimidazolines, and asparagine derivatives.

The alkyl group in these surface-active agents preferably is a group having from 1 to 22 carbon atoms.

In these shampoos, the concentration of surface-active agent is generally from 3 to 50% by weight and preferably from 3 to 20%, and the pH is generally from 3 to 10.

If the compositions for the hair, according to the invention, are rinse-off lotions, they can be aqueous or aqueous-alcoholic solutions, emulsions, thickened lotions or gels.

If the compositions are emulsions, they may be non-ionic or anionic. The non-ionic emulsions consist mainly of a mixture of oil and/or fatty alcohol with a polyoxyethyleneated alcohol such as polyoxyethyleneated stearyl or cetyl-stearyl alcohol. Cationic surface-active agents, such as those defined above, can be added to these compositions.

The anionic emulsions are essentially based on soaps.

If the compositions are gels or thickened lotions, they contain thickeners in the presence or absence of solvents. The thickeners which can be used include sodium alginate, gum arabic or cellulose derivatives such as methylcellulose, hydroxymethylcellulose, hydroxyethylcellulose, hydroxypropylcellulose, hydroxypropylmethylcellulose or carboxymethylcellulose. The lotions can also be thickened with a mixture of polyethylene glycol and polyethylene glycol stearate or distearate or with a mixture of a phosphoric acid ester and an amide. The concentration of thickener can vary from 0.5 to 30% by weight, preferably from 0.5 to 15% by weight and more preferably from 0.5 to 5%. The pH of the rinse-off lotions may be from 3 to 9 and preferably from 4.5 to 7.5.

Compositions which are rinse-off lotions can also contain surface-active agents, such as those mentioned above, generally in proportions of from 0.1 to 30%.

If the compositions for the hair, are styling lotions, shaping lotions, so-called setting lotions or lacquers, they generally contain at least one active compound of formula (I) together with polymers if appropriate, in aqueous, alcoholic or aqueous-alcoholic solution.

The aqueous-alcoholic lotions generally contain from 10 to 70% by weight of a lower alcohol having from 1 to 4 carbon atoms, preferably ethanol or isopropanol, relative to the total weight of the composition.

Examples of polymers which can be used are: polyvinylpyrrolidone, copolymers of polyvinylpyrrolidone and vinyl acetate, copolymers of vinyl acetate and an unsaturated carboxylic acid such as crotonic acid, copolymers resulting from the polymerization of vinyl acetate, crotonic acid and an acrylic or methacrylic acid ester, copolymers resulting from the copolymerization of vinyl acetate, an alkyl vinyl ether and an unsaturated carboxylic acid, and copolymers resulting from the copolymerization of vinyl acetate, crotonic acid and a vinyl ester of an acid with a long carbon chain or alternatively an allyl or methallyl ester of an acid with a long carbon chain. Preferably their concentration is from 0.1 to 5% by weight, relative to the total weight of the composition.

These compositions can also be pressurized as an aerosol. The propellant gas used may be carbon dioxide, nitrogen, nitrous oxide, volatile hydrocarbons such as butane, isobutane and propane, and chlorohydrocarbons or fluorohydrocarbons, preferably the Freons.

The compositions according to the invention can also contain any other ingredient normally used in cosmetics, such as perfumes, colourants, preservatives, sequestering agents, thickeners, softeners, foam synergistic agents and/or stabilizers, sun filters, peptizing agents, pigments, fatty alcohols, waxes and humectants.

The compositions for the hair, according to the invention, can also be shampoos in powder or aerosol form, which are applied to the hair when dry, left on the hair for a certain time after application and the hair is then simply brushed.

If the cosmetic compositions are intended to be applied to the skin, they are generally emulsions such as creams or milks, gels, skin packs, aerosol foams, or aqueous or aqueous-alcoholic lotions. The aqueous-alcoholic lotions preferably contain an alcohol having from 1 to 4 carbon atoms, preferably ethanol or isopropanol, preferably in a proportion of 10 to 70% by weight, relative to the total weight of the composition.

They can also contain any ingredient conventionally used in beauty creams for the face, such as fatty substances, emulsifying agents, preservatives, perfumes, colourants, and waxes. They can also contain coloured pigments making it possible to colour the epidermis and mask skin imperfections.

These compositions which can be applied to the skin also make it possible to carry out a process for improving the appearance of the skin in which a composition such as defined above is applied to those parts of the epidermis which it is desired to treat.

The invention will be understood more clearly with the aid of the examples which follow, in which the parts and percentages are by weight unless stated otherwise. A.I. where used stands for "Active Ingredient".

EXAMPLE 1

The following shampoo is prepared:

| | |
|---|---|
| Triethanolamine alkyl($C_{12}$–$C_{14}$)—sulphate | 8 g AI* |
| Hydroxyethylcellulose sold by HERCULES under the trademark "Natrosol 250 HHR" | 0.5 g |
| Potassium salt of 3,4-dihydro-6-methyl-1,2,3-oxathiazin-4-one 2,2-dioxyde, having the formula | 5 g |

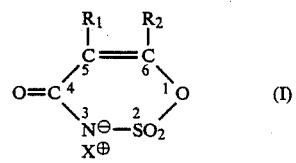

wherein $R_1$ is hydrogen, $R_2$ is methyl pH = 6.5
Water q.s. (quantity sufficient for)   100 g

EXAMPLE 2

The following shampoo is prepared:

| | |
|---|---|
| Alkyl($C_{12}$–$C_{18}$)dimethylcarboxymethylammonium hydroxide sold by HENKEL under the trademark "DEHYTON AB 30" | 4 g AI |
| $CH_3$—$(CH_2)_{11}$—$CH_2$—$(OCH_2CH_2)_6$—$OCH_2$—COONa sold by SANDOZ under the trademark "SANDOPAN DTC AC" | 8 g AI |
| Potassium salt of 3,4-dihydro-6-methyl-1,2,3-oxathiazin-4-one 2,2-dioxide | 5 g |
| pH = 5.9 | |
| Water q.s. | 100 g |

*AI: active ingredient.

EXAMPLE 3

The following shampoo is prepared:

| | |
|---|---|
| Glycoside alkyl ether sold by SEPPIC under the trademark "TRITON CG 110" | 4.6 g AI |
| $CH_3$—$(CH_2)_{11}$—$CH_2$—$(OCH_2CH_2)_6$—$OCH_2$—COONa sold by SANDOZ under the trademark "SANDOPAN DTC AC" | 4.6 g AI |
| Potassium salt of 3,4-dihydro-6-methyl-1,2,3-oxathiazin-4-one 2,2-dioxide | 5 g |
| Carboxymethylcellulose | 0.5 g |
| pH = 5.5 | |
| Water q.s. | 100 g |

EXAMPLE 4

The following shampoo is prepared:

| | |
|---|---|
| Mixed sodium and triethanolamine salts of lipoaminoacids obtained by combining Lauric acid with the aminoacids produced by the total hydrolysis of collagen, sold by RHONE-POULENC under the trademark "LIPOPROTEOL LCO" | 4.4 g AI |
| R—CHOH—CH$_2$—O(CH$_2$—CHOH—CH$_2$—O)$_n$H (R = mixture of C$_9$–C$_{12}$alkyl radicals) (n = average statistical value of about 3.5) | 7 g |
| Carboxymethylcellulose | 0.5 g |
| Potassium salt of 3,4-dihydro-6-methyl-1,2,3-oxathiazin-4-one 2,2-dioxide | 4.7 g |
| pH = 7 | |
| Water q.s. | 100 g |

EXAMPLE 5

The following shampoo is prepared:

| | |
|---|---|
| Triethanolamine alkyl(C$_{12}$–C$_{14}$)-sulphate | 8 g AI |
| Carboxymethylcellulose | 0.5 g |
| Potassium salt of 3,4-dihydro-6-methyl-1,2,3-oxathiazin-4-one 2,2-dioxide | 5 g |
| pH = 6.8 | |
| Water q.s. | 100 g |

EXAMPLE 6

A foaming rinse-off lotion for greasy hair, packaged in the form of an aerosol, is prepared:

| | |
|---|---|
| Glycoside alkyl ether sold by SEPPIC under the trademark "TRITON CG 110" | 0.5 g AI |
| Potassium salt of 3,4-dihydro-6-methyl-1,2,3-oxathiazin-4-one 2,2-dioxide | 5 g |
| Perfume | 0.5 g |
| Preservative | 0.2 g |
| Water q.s. | 100 g |

90 g of the above composition are introduced into an aerosol container together with 10 g of Freon F 12.

EXAMPLE 7

The following rinse-off gel for greasy hair is prepared:

| | |
|---|---|
| Carboxymethylcellulose | 3 g |
| Cetyl alcohol | 0.5 g |
| Potassium salt of 3,4-dihydro-6-methyl-1,2,3-oxathiazin-4-one 2,2-dioxide | 3 g |
| Perfume | 1 g |
| Preservative | 0.3 g |
| Lactic acid q.s. pH = 7 | |
| Water q.s. | 100 g |

EXAMPLE 8

A hair shaping lotion (leave-on) for greasy hair is prepared:

| | |
|---|---|
| Polyvinylpyrrolidone/vinyl acetate copolymer (PVP/VA: 60%/40%) | 0.2 g AI |
| Ethyl alcohol | 35 g |
| Potasssium salt of 3,4-dihydro-6-methyl-1,2,3-oxathiazin-4-one 2,2-dioxide | 1 g |
| Perfume | 0.7 g |
| Preservative | 0.2 g |
| pH = 7.9 | |
| Water q.s. | 100 g |

EXAMPLE 9

A leave-on hair lotion is prepared:

| | |
|---|---|
| Potassium salt of 3,4-dihydro-6-methyl-1,2,3-oxathiazin-4-one 2,2-dioxide | 1 g |
| Preservative | 0.2 g |
| Perfume | 0.4 g |
| Colourant | 0.2 g |
| pH = 7 | |
| Water q.s. | 100 g |

EXAMPLE 10

A cream for greasy skin is prepared:

| | |
|---|---|
| Beeswax | 2 g |
| Stearyl alcohol | 1 g |
| Cetyl alcohol | 1 g |
| Potassium salt of 3,4-dihydro-6-methyl-1,2,3-oxathiazin-4-one 2,2-dioxide | 1 g |
| Hydroxyethylcellulose sold by HERCULES under the trademark "Natrosol 250 HHR" | 1 g |
| Perfume | 0.3 g |
| Preservative | 0.1 g |
| pH = 5.8 | |
| Water q.s. | 100 g |

EXAMPLE 11

A milk for greasy skin is prepared:

| | |
|---|---|
| Mixture of cetyl-stearyl alcohol and cetyl-stearyl alcohol oxyethyleneated with 15 mol of ethylene oxide | 2 g AI |
| Stearyl alcohol | 1 g |
| Cetyl alcohol | 1 g |
| Potassium salt of 3,4-dihydro-6-methyl-1,2,3-oxathiazin-4-one 2,2-dioxide | 1 g |
| Carboxymethylcellulose | 1 g |
| Perfume | 0.2 g |
| Preservative | 0.15 g |
| pH = 6.3 | |
| Water q.s. | 100 g |

EXAMPLES 12–22

These examples correspond to Examples 1–11 except that, as the oxathiazinone derivative of the formula (I), the potassium salt of 3,4-dihydro-6-methyl-1,2,3-oxathiazin-4-one 2,2-dioxide is replaced by the same weight of the potassium salt of 3,4-dihydro-5,6-dimethyl-1,2,3-oxathiazin-4-one 2,2-dioxide.

EXAMPLES 23–33

These examples are identical to Examples 1–11 except that the potassium salt of 3,4-dihydro-6-methyl-1,2,3-oxathiazin-4-one 2,2-dioxide is replaced with the same weight of the potassium salt of 3,4-dihydro-5-ethyl-6-methyl-1,2,3-oxathiazin-4-one 2,2-dioxide.

We claim:

1. A cosmetic composition suitable for treating greasy hair or skin, which comprises,
   in a cosmetically acceptable vehicle, from about 0.05% to 20% by weight of at least one oxathiazinone derivative of the formula:

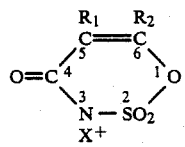

in which
R$_1$ denotes hydrogen or an alkyl radical having from 1 to 4 carbon atoms;
R$_2$ denotes an alkyl radical having from 1 to 4 carbon atoms; and
X denotes an alkali metal; and
at least one cosmetic adjuvant selected from the group consisting of non-ionic, anionic, cationic, and amphoteric surface active agents and mixtures thereof, thickeners, cosmetic polymers, preservatives, sequestering agents, foam snynergistic agents, foam stabilizers, sun filters, colourants, pigments, fatty alcohols, waxes, humectants and perfumes.

2. A composition according to claim 1, in which X denotes potassium.

3. A composition according to claim 1 which contains from 0.5 to 5% by weight of at least one oxathiazinone derivative relative to the total weight of the composition.

4. A composition according to claim 1 which contains from 3 to 50% by weight of surface-active agent, relative to the total weight of the composition.

5. A composition according to claim 1 which contains from 3 to 20% by weight of a surface-active agent, relative to the total weight of the composition.

6. A composition according to claim 1 which contains from 0.5 to 30% by weight of thickener, relative to the total weight of the composition.

7. A composition according to claim 1 which contains 0.5 to 5% by weight of thickener, relative to the total weight of the composition.

8. A composition according to claim 1, which contains from 0.1 to 5% by weight of at least one cosmetic polymer, relative to the total weight of the composition.

9. A composition according to claim 1 in which the vehicle is water, a lower alcohol or a mixture of water and lower alcohol, the lower alcohol having from 1 to 4 carbon atoms.

10. A composition according to claim 9 in which the mixture of alcohol and water contains 10 to 70% by weight of alcohol relative to the total weight of the composition.

11. A composition according to claim 1, in the form of a suspension, a solution, an emulsion, a gel or a powder.

12. A composition according to claim 1 in the form of a shampoo, a rinse-off lotion or a cream, a setting lotion, a blow-drying lotion a lacquer.

13. A composition according to claim 1, in the form of an emulsion, a gel, an aerosol foam, or an aqueous or aqueous-alcoholic lotion.

14. A composition according to claim 1 wherein said oxathiazinone derivative is an aqueous solution of oxathiazinone.

15. A cosmetic composition suitable for treating greasy hair or skin, which comprises, in a cosmetically acceptable vehicle, from about 0.05% to 20% by weight of at least one oxathiazinone derivative of the formula

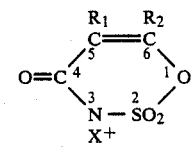

in which
R$_1$ denotes hydrogen or an alkyl radical having from 1 to 4 carbon atoms;
R$_2$ denotes an alkyl radical having from 1 to 4 carbon atoms; and
X denotes an alkali metal; and
an effective amount of an anionic, non-ionic, cationic, amphoteric surface-active agent or a mixture thereof.

16. The composition of claim 15 and further comprising an effective amount of a thickener.

17. The composition of claim 15 and further comprising an effective amount of a polymer.

18. The composition of claim 15 and further comprising an effective amount of a preservative.

19. The composition of claim 15 and further comprising an effective amount of a sequestering agent.

20. The composition of claim 15 and further comprising an effective amount of a sun filter.

21. The composition of claim 15 and further comprising an effective amount of a colourant.

22. The composition of claim 15 and further comprising an effective amount of a fatty alcohol or a wax.

23. The composition of claim 15 and further comprising an effective amount of a humectant.

24. The composition of claim 15 wherein in the formula of the oxathiazinone derivative R$_1$ denotes hydrogen and R$_2$ denotes CH$_3$.

25. The composition of claim 16 wherein in the formula of the oxathiazinone derivative R$_1$ denotes hydrogen and R$_2$ denotes CH$_3$.

26. The composition of claim 17 wherein in the formula of the oxathiazinone derivative R$_1$ denotes hydrogen and R$_2$ denotes CH$_3$.

27. The composition of claim 18 wherein in the formula of the oxathiazinone derivative R$_1$ denotes hydrogen and R$_2$ denotes CH$_3$.

28. The composition of claim 19 wherein in the formula of the oxathiazinone derivative R$_1$ denotes hydrogen and R$_2$ denotes CH$_3$.

29. The composition of claim 20 wherein in the formula of the oxathiazinone derivative R$_1$ denotes hydrogen and R$_2$ denotes CH$_3$.

30. The composition of claim 21 wherein in the formula of the oxathiazinone derivative R$_1$ denotes hydrogen and R$_2$ denotes CH$_3$.

31. The composition of claim 22 wherein in the formula of the oxathiazinone derivative R$_1$ denotes hydrogen and R$_2$ denotes CH$_3$.

32. The composition of claim 23 wherein in the formula of the oxathiazinone derivative R$_1$ denotes hydrogen and R$_2$ denotes CH$_3$.

33. A shampoo composition for treating greasy hair or skin which comprises, in a cosmetically acceptable vehicle, from about 0.05% to 20% by weight of at least one oxathiazinone derivative of the formula

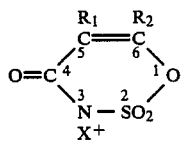

in which
- $R_1$ denotes hydrogen or an alkyl radical having from 1 to 4 carbon atoms;
- $R_2$ denotes an alkyl radical having from 1 to 4 carbon atoms; and
- X denotes an alkali metal;

and at least one anionic, non-ionic, cationic or amphoteric surface-active agent, or a mixture thereof in an amount ranging from 3 to 50% by weight.

34. A setting lotion or a lacquer composition for treating greasy hair or skin, which comprises in an aqueous, alcoholic or aqueous-alcoholic vehicle from about 0.05% to 20% by weight of at least one oxathiazinone derivative of the formula

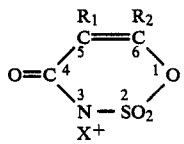

in which
- $R_1$ denotes hydrogen or an alkyl radical having from 1 to 4 carbon atoms;
- $R_2$ denotes an alkyl radical having from 1 to 4 carbon atoms; and
- X denotes an alkali metal;

and at least one cosmetic polymer present in an amount of 0.1% to 5% by weight.

35. The composition of claim 33 wherein in the formula of the oxathiazinone derivative $R_1$ denotes hydrogen and $R_2$ denotes $CH_3$.

36. The composition of claim 34 wherein in the formula of the oxathiazinone derivative $R_1$ denotes hydrogen and $R_2$ denotes $CH_3$.

37. A method for treating greasy hair and skin comprising applying to greasy hair and skin a composition comprising from about 0.05 to about 20% of at least one oxathiazinone derivative of the formula:

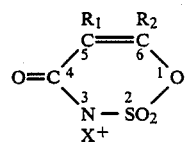

in which
- $R_1$ denotes hydrogen, an alkyl radical having from 1 to 20 carbon atoms, an aryl radical having up to 10 carbon atoms, or an acyl radical $R_3CO$, in which $R_3$ is an alkyl radical having from 2 to 4 carbon atoms;
- $R_2$ denotes an alkyl radical having from 1 to 20 carbon atoms or an aryl radical having up to 10 carbon atoms; or
- $R_1$ and $R_2$ together with the carbon atoms to which they are attached form an alicyclic radical having up to 10 carbon atoms, which is unsubstituted or substituted by one or more hydrocarbon radicals; and
- X denotes an alkali metal.

38. A method according to claim 37, wherein X denotes potassium.

39. A method according to claim 37, wherein $R_1$ denotes hydrogen or an alkyl radical having from 1 to 4 carbon atoms and $R_2$ denotes an alkyl radical having from 1 to 4 carbon atoms.

40. A method according to claim 39, wherein $R_1$ denotes hydrogen, $R_2$ denotes $CH_3$ and X denotes potassium.

41. A method according to claim 37, wherein from 0.05 to 20% by weight of said at least one oxathiazinone derivative is present in said cosmetically suitable vehicle.

42. A method according to claim 37, wherein said cosmetically acceptable vehicle is water, a lower alcohol or a mixture of water and lower alcohol, the lower alcohol having from 1 to 4 carbon atoms.

43. A method according to claim 42, wherein said mixture of alcohol and water contains 10 to 70% by weight of alcohol relative to the total weight of the composition.

44. A method according to claim 37, wherein the composition is in the form of a suspension, a solution, an emulsion, a gel or a powder.

45. A method according to claim 37, wherein the composition is in the form of a shampoo, a rinse-off lotion, a cream, a setting lotion, a blow-drying lotion, or a lacquer.

46. A method according to claim 37 wherein the composition is in the form of an aerosol foam, or an aqueous or aqueous-alcoholic lotion.

* * * * *